US012693259B2

(12) United States Patent
Okamoto et al.

(10) Patent No.: US 12,693,259 B2
(45) Date of Patent: Jul. 28, 2026

(54) IN VITRO DIAGNOSIS METHOD FOR PERIODONTAL DISEASES, AND Pg BACTERIUM DETECTION METHOD

(71) Applicant: NATIONAL INSTITUTE FOR MATERIALS SCIENCE, Tsukuba (JP)

(72) Inventors: Akihiro Okamoto, Tsukuba (JP); Divya Naradasu, Tsukuba (JP)

(73) Assignee: National Institute for Materials Science, Tsukuba (JP)

( * ) Notice: Subject to any disclaimer, the term of this patent is extended or adjusted under 35 U.S.C. 154(b) by 300 days.

(21) Appl. No.: 18/569,549

(22) PCT Filed: Jun. 21, 2022

(86) PCT No.: PCT/JP2022/024727
§ 371 (c)(1),
(2) Date: Dec. 12, 2023

(87) PCT Pub. No.: WO2023/276785
PCT Pub. Date: Jan. 5, 2023

(65) Prior Publication Data
US 2024/0385140 A1 Nov. 21, 2024

(30) Foreign Application Priority Data
Jun. 29, 2021 (JP) ................................. 2021-107163

(51) Int. Cl.
*G01N 27/416* (2006.01)
*G01N 27/327* (2006.01)
(Continued)

(52) U.S. Cl.
CPC ......... *G01N 27/416* (2013.01); *G01N 27/327* (2013.01); *G01N 33/56955* (2013.01);
(Continued)

(58) Field of Classification Search
CPC .............. G01N 27/416; G01N 27/327; G01N 27/3272; G01N 33/56955; G01N 33/48735; G01N 2800/18; G01N 2800/26
See application file for complete search history.

(56) References Cited

FOREIGN PATENT DOCUMENTS

| | | |
|---|---|---|
| JP | 2007-84534 A | 4/2007 |
| JP | 2018-142541 A | 9/2018 |

(Continued)

OTHER PUBLICATIONS

Sato et al., "An Electrochemical Protease Assay Using Ferrocenylpeptide for Screening of Periodontal Disease," Bunseki Kagaku, vol. 70(2021), pp. 199-206 (Year: 2021).*

(Continued)

*Primary Examiner* — Alexander S Noguerola
(74) *Attorney, Agent, or Firm* — SALIWANCHIK, LLOYD & EISENSCHENK

(57) ABSTRACT

The in vitro diagnostic method for periodontal disease of the present invention includes bringing a sample derived from an oral cavity of a subject into contact with an electrode to perform electrochemical measurement in the presence of a glucogenic amino acid and an electron mediator under an anaerobic environment and providing information for judging that periodontal disease is progressing in the oral cavity of the subject when current generation is detected as a result of the electrochemical measurement. According to the in vitro diagnostic method for periodontal disease of the present invention, it is possible to provide information for judging the progress of periodontal disease by simple operation.

20 Claims, 8 Drawing Sheets

(51) Int. Cl.
    *G01N 33/569* (2006.01)
    *G01N 33/487* (2006.01)
(52) U.S. Cl.
    CPC ... *G01N 33/48735* (2013.01); *G01N 2800/18* (2013.01); *G01N 2800/26* (2013.01)

(56) References Cited

FOREIGN PATENT DOCUMENTS

| WO | WO 0104626 A1 * | 1/2001 | ............ G01N 33/18 |
| WO | 2004/106541 A1 | 12/2004 | |

OTHER PUBLICATIONS

Google machine-generated English language translation of Sato et al., "An Electrochemical Protease Assay Using Ferrocenylpeptide for Screening of Periodontal Disease," Bunseki Kagaku, vol. 70(2021), pp. 199-206 (Year: 2021).*

Fiveable general biology review website defintion of "obligate anaerobes", 2025, https://fiveable.me/key-terms/college-bio/obligate-anaerobes (Year: 2025).*

Naradasu et al., "Electrochemical Characterization of Current-Producing Human Oral Pathogens by Whole-Cell Electrochemistry," ChemEfectroChem 2020, 7, 2012-2019 (Year: 2020).*

IEnglish language translation of International Preliminary Report on Patentability for English language translation , issued Dec. 14, 2023 (Year: 2023).*

Gamry Instruments—"Physical Electrochemistry Software", 2018 (Year: 2018).*

'Chronocoulometry' in IUPAC Compendium of Chemical Terminology, 5th ed. International Union of Pure and Applied Chemistry; 2025. Online version 5.0.0, 2025 (Year: 2025).*

Park et al., Washing- and Separation-Free Electrochemical Detection of Porphyromonas gingivalis in Saliva for Initial Diagnosis of Periodontitis, with Supporting Information, Anal. Chem. 2021, 93, 5644-5650 (Year: 2021).*

Supplementary European Search Report dated May 19, 2025 in European Application No. 22832933.0.

Office Action dated May 7, 2025 in Japanese Application No. 2023-531840.

Office Action dated Jan. 21, 2025 in Japanese Application No. 2023-531840.

International Search Report dated Aug. 23, 2022 in International Application No. PCT/JP2022/024727.

Park, S. et al., "Washing- and Separation-Free Electrochemical Detection of Porphyromonas gingivalis in Saliva for Initial Diagnosis of Periodontitis," Analytical Chemistry, 2021, 93:5644-5650, American Chemical Society.

* cited by examiner

FIG. 2

IN VITRO DIAGNOSIS METHOD FOR PERIODONTAL DISEASES, AND Pg BACTERIUM DETECTION METHOD

CROSS-REFERENCE TO RELATED APPLICATIONS

This application is the U.S. national stage application of International Patent Application No. PCT/JP2022/024727, filed Jun. 21, 2022, which claims the benefit under 35 U.S.C. § 119 of Japanese Application No. 2021-107163, filed Jun. 29, 2021, the disclosures of each of which are incorporated herein by reference in their entirety.

TECHNICAL FIELD

The present invention relates to an in vitro method for diagnosing periodontal disease and a Pg bacterium detection method.

BACKGROUND ART

Periodontal disease is a general term for disease in the periodontal tissue, which is the tissue supporting teeth, and is thought to be multifactorial disease that is caused by various factors. Among these large number of factors, one of main factors is infection of a periodontal pocket with periodontopathogenic bacteria. Such bacterial infection causes the destruction of periodontal tissue, eventually resulting in tooth loss.

It is known that a large number of periodontopathogenic bacteria are present, and it is thought that among them, *Porphyromonas gingivalis* (hereinafter, also referred to as "Pg bacteria"), Tannerella forsythia (hereinafter, also referred to as "Tf bacteria"), and *Treponema denticola* (hereinafter, also referred to as "Td bacteria") have a high possibility of becoming pathogenic bacteria of periodontal disease and are further involved in not only periodontal disease but also disease of other organs, and in vitro diagnostic methods for detecting the activity of these bacteria in the oral cavities of subjects are being investigated.

As one of the methods, it is known a method of utilizing the fact that the above-described periodontopathogenic bacteria (Pg bacteria, Tf bacteria, and Td bacteria) have a trypsin-like enzyme activity. That is, the method is technology for diagnosing periodontal disease by detecting the above enzyme activity. For example, PTL 1 describes "a periodontal disease detection method characterized by using a cysteine protease that is produced by *gingivalis* bacteria as a periodontal disease marker for detecting periodontal disease".

CITATION LIST

Patent Literature

PTL 1: International Publication No. WO 2004/106541

SUMMARY OF INVENTION

Technical Problem

The periodontal disease detection method described in PTL 1 measures the enzyme activity. The activity varies greatly depending on the reaction temperature, and the measurement procedure is complicated, so that skill is required for the measurement, and there is room for improvement.

Accordingly, an object of the present invention is to provide an in vitro diagnostic method for periodontal disease, which can provide information for judging progress of periodontal disease by simple operation. In addition, an object of the present invention is to provide a Pg bacterium detection method.

Solution to Problem

The present inventors have made intensive studies to achieve the above objects and, as a result, found that the above objects can be achieved by the following configurations.

[1] An in vitro diagnostic method for periodontal disease, comprising bringing a sample derived from an oral cavity of a subject into contact with an electrode to perform electrochemical measurement in the presence of a glucogenic amino acid and an electron mediator under an anaerobic environment, and providing information for judging that periodontal disease is progressing in the oral cavity of the subject when current generation is detected as a result of the electrochemical measurement.

[2] The in vitro diagnostic method for periodontal disease according to [1], wherein the glucogenic amino acid includes at least one selected from the group consisting of arginine, histidine, aspartic acid, and glutamic acid.

[3] The in vitro diagnostic method for periodontal disease according to [1] or [2], wherein the electron mediator includes at least one selected from the group consisting of flavin mononucleotide, riboflavin, and 2-hydroxy-1,4-naphthoquinone.

[4] The in vitro diagnostic method for periodontal disease according to any one of [1] to [3], wherein the electron mediator is 2-hydroxy-1,4-naphthoquinone.

[5] The in vitro diagnostic method for periodontal disease according to any one of [1] to [4], wherein the method of the electrochemical measurement is a method by controlling a potential of the electrode and measuring a current flowing in the electrode as a function of time.

[6] The in vitro diagnostic method for periodontal disease according to [5], wherein the potential is within a range of greater than 0 V with respect to a silver-silver chloride electrode and less than the upper limit of a potential window.

[7] The in vitro diagnostic method for periodontal disease according to any one of [1] to [6], wherein the information for the judgement includes at least one measurement result selected from the group consisting of a time from start of the electrochemical measurement to detection of the current generation and a maximum value of current density of the generated current.

[8] The in vitro diagnostic method for periodontal disease according to [7], wherein the information for the judgement includes comparison information between a predetermined reference value and the measurement result.

[9] The in vitro diagnostic method for periodontal disease according to any one of [1] to [8], wherein the pathogenic bacteria of the periodontal disease includes *Porphyromonas gingivalis*.

[10] A Pg bacterium detection method comprising bringing a sample into contact with an electrode to perform electrochemical measurement in the presence of a glucogenic amino acid and 2-hydroxy-1,4-naphthoquinone under an anaerobic environment, and providing information for judging that *Porphyromonas gingivalis* is contained in the sample when current generation is detected as a result of the electrochemical measurement.

[11] The Pg bacterium detection method according to [10], wherein the method of the electrochemical measurement is a method by controlling a potential of the electrode and measuring a current flowing in the electrode as a function of time.

[12] The Pg bacterium detection method according to [11], wherein the potential is within a range of greater than 0 V with respect to a silver-silver chloride electrode and less than the upper limit of a potential window.

[13] The Pg bacterium detection method according to any one of [10] to [12], wherein the information for the judgement includes at least one measurement result selected from the group consisting of a time from start of the electrochemical measurement to detection of the current generation and a maximum value of current density of the generated current.

[14] The Pg bacterium detection method according to [13], wherein the information for the judgement includes comparison information between a predetermined reference value and the above measurement result.

Advantageous Effects of Invention

The in vitro diagnostic method of the present invention includes bringing a sample derived from an oral cavity of a subject into contact with an electrode to perform electrochemical measurement in the presence of a glucogenic amino acid and an electron mediator under an anaerobic environment, and providing information for judging that periodontal disease is progressing in the oral cavity of the subject when current generation is detected as a result of the electrochemical measurement. According to this method, information for judging progress of periodontal disease can be obtained by simple operation of electrochemical measurement of a sample in the presence of a glucogenic amino acid and an electron mediator.

When the glucogenic amino acid includes at least one selected from the group consisting of arginine, histidine, aspartic acid, and glutamic acid, the resulting generation current tends to be larger. Consequently, measurement with higher sensitivity is possible, and as a result, more accurate information can be obtained.

When the electron mediator includes at least one selected from the group consisting of flavin mononucleotide (FMN), riboflavin (RF), and 2-hydroxy-1,4-naphthoquinone (hereinafter, also referred to as "HNQ"), the flow of electrons that are transferred to an electrode by metabolism of periodontopathogenic bacteria tends to be smoother. In other words, electrons are more likely to be withdrawn from periodontopathogenic bacteria by the specific electron mediator. As a result, larger current generation is obtained, and the dynamic range becomes greater.

The above-mentioned tendency is significant particularly when the electron mediator includes HNQ. The present inventors have confirmed experimentally that when the electron mediator includes HNQ, surprisingly, the time until the detection of current generation is also shortened. That is, the time until providing information can be more shortened.

When the method of the electrochemical measurement is a method by controlling the potential of an electrode and measuring the current flowing in the electrode as a function of time, the current generation is more likely to be detected, and as a result, more accurate information is likely to be obtained.

When the controlled potential of the electrode is within a range greater than 0 V (vs. Ag/AgCl: silver-silver chloride electrode) and less than the upper limit of the potential window, the flow of electrons that are transferred from the periodontopathogenic bacteria to the electrode through the electron mediator becomes smoother, and more accurate measurement becomes possible.

When the information for the judgement includes at least one measurement result selected from the group consisting of a time from start of the electrochemical measurement to detection of the current generation and a maximum value of current density of the generated current, which is preferable in that the quantitative evaluation is easier. For example, when samples are collected from the same subject several times over time, it is also possible to determine the progress of periodontal disease in chronological order by comparing the obtained information.

When the information for the judgement includes comparison information between a predetermined reference value and the above measurement result, for example, the judgement of progress of periodontal disease becomes easier by using a reference value determined for each subject. In addition, when a reference value determined for each of attributes of a subject, such as age and gender, is used, since the comparison target becomes clear even with a single measurement, the degree of progress of periodontal disease is easily judged from the obtained information.

The Pg bacterium detection method of the present invention includes bringing a sample into contact with an electrode to perform electrochemical measurement in the presence of a glucogenic amino acid and HNQ under an anaerobic environment and providing information for judging that the sample contains Pg bacteria when current generation is detected as a result of the electrochemical measurement.

According to the above method, since HNQ is used as an electron mediator, even if the sample contains contaminants and/or other bacteria, it is possible to specifically detect Pg bacteria by simple operation. Since Pg bacteria as periodontopathogenic bacteria can be detected even if operation such as culture is not performed, the method can be easily applied to, for example, the decision of dental treatment policy.

When the method of the electrochemical measurement is a method by controlling the potential of the electrode and measuring the current flowing in the electrode as a function of time, the current generation by Pg bacteria is more likely to be detected, and as a result, more accurate information is likely to be obtained.

When the controlled potential of the electrode is within a range greater than 0 V (vs. Ag/AgCl) and less than the upper limit of the potential window, the flow of electrons that are transferred from Pg bacteria to the electrode through HNQ becomes smoother, and more accurate measurement becomes possible.

When the information for the judgement includes at least one measurement result selected from the group consisting of a time from start of the electrochemical measurement to detection of the current generation and a maximum value of current density of the generated current, which is preferable in that the quantitative evaluation is easier. For example, it is possible to compare the numbers of Pg bacteria between samples.

When the information for the judgement includes comparison information between a predetermined reference value and the measurement result, for example, more accurate measurement is possible by creating a reference value based on a blank sample.

BRIEF DESCRIPTION OF DRAWINGS

FIG. 2 is a chronoamperogram showing the influence of histidine on a generation current.

DESCRIPTION OF EMBODIMENTS

The present invention will now be described in detail.

The description of the constituent elements described below may be made based on representative embodiments of the present invention, but the present invention is not limited to such embodiments.

In the present specification, the numerical range expressed using "to" means a range that includes the numerical values described before and after "to" as lower and upper limits.

[In Vitro Diagnostic Method]

Figure 1:
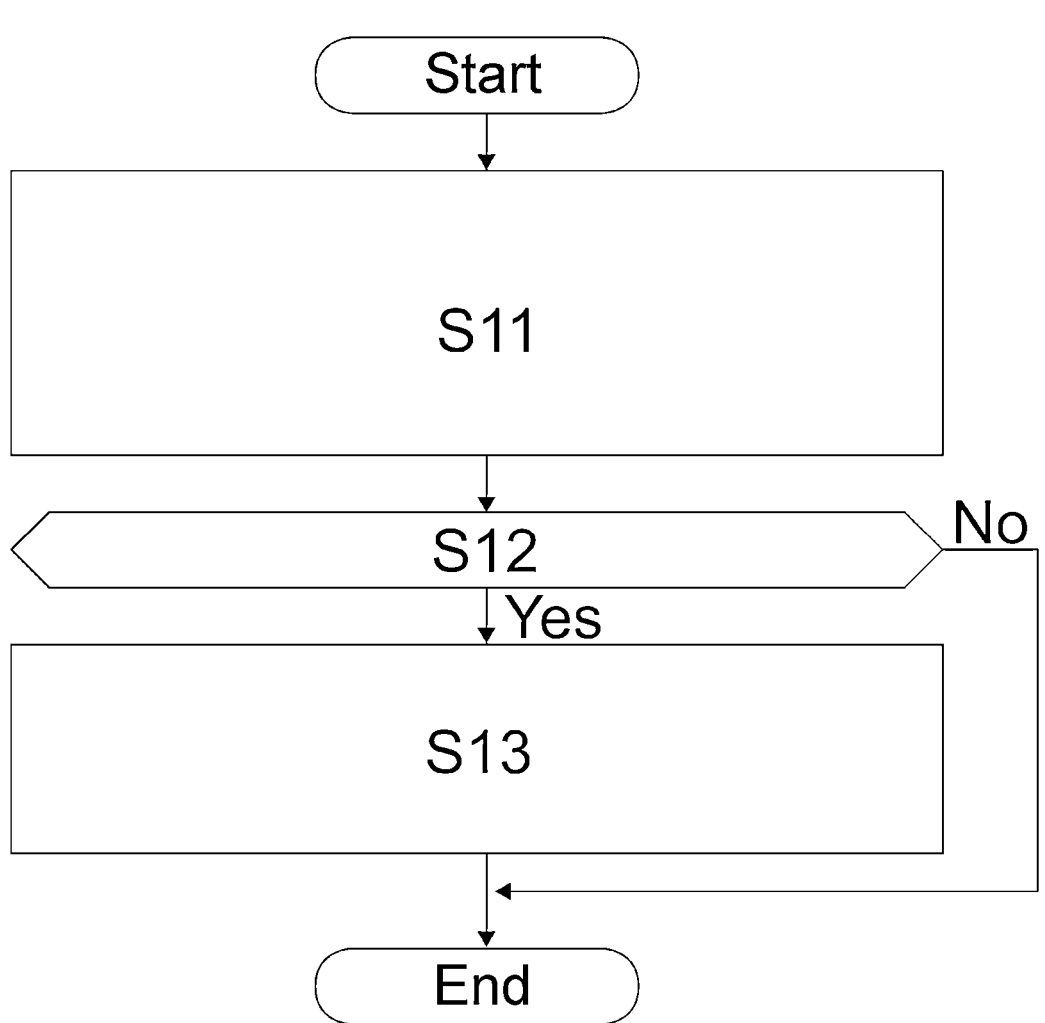
FIG. 1 is a flow chart of an in vitro diagnostic method according to an embodiment of the present invention.

FIG. 1 is a flow chart of an in vitro diagnostic method according to an embodiment of the present invention.

First, a sample derived from an oral cavity of a subject is brought into contact with an electrode, and electrochemical measurement is performed in the presence of a glucogenic amino acid and an electron mediator under an anaerobic environment (Step S11).

The sample is not particularly limited as long as it is derived from the inside of an oral cavity of a subject, and preferably includes saliva, plaque, blood, and pus and a mixture thereof. In particular, when a sample includes saliva, which is preferable in that it is more noninvasive and the collection is easier.

The sample may include water and an electrolyte or the like as components other than the above.

The electrolyte is not particularly limited, and a known electrolyte can be used. However, the electrolyte preferably does not include organic substance other than the glucogenic amino acid described later.

The electrochemical measurement is performed in the presence of a glucogenic amino acid. The performing of the electrochemical measurement in the presence of a glucogenic amino acid is typically, for example, a form of adding a glucogenic amino acid to a sample.

Examples of the glucogenic amino acid include alanine, glycine, serine, threonine, cysteine, tryptophane, isoleucine, methionine, valine, aspartic acid, arginine, glutamic acid, histidine, proline, tyrosine, and phenylalanine. Among them, from the viewpoint that the generation current (density) tends to be larger, at least one selected from the group consisting of arginine, histidine, aspartic acid, and glutamic acid is preferable, and at least one selected from the group consisting of arginine and histidine is more preferable.

Histidine has higher water solubility compared to aspartic acid and glutamic acid and is preferable in that it tends to become more uniform even when added to a sample. If the water-solubility is high, it is not required to add an acid or the like to a sample. Accordingly, it is also preferable in that the background current in the measurement tends to become small.

The present inventors have confirmed experimentally that when the glucogenic amino acid is histidine, the generation current derived from Pg bacteria tends to become greater (see Examples).

When aspartic acid or glutamic acid is used as the glucogenic amino acid, a more uniform sample can be obtained by adding an acid (for example, hydrochloric acid) to a sample to adjust the pH to 6.0 or less (for example, about 5.2).

The content of the glucogenic amino acid in the sample is not particularly limited and is generally preferably 0.1 to 1000 mM.

The electrochemical measurement is performed in the presence of an electron mediator. Although some of periodontopathogenic bacteria have a function of generating a current under an anaerobic environment and transferring the current to an extracellular electron acceptor (e.g., anode electrode), the electrochemical measurement in the presence of an electron mediator is more preferable because the electron transfer can be performed more smoothly.

The performing of the electrochemical measurement in the presence of an electron mediator is, as in the case of the glucogenic amino acid, typically, a form of adding an electron mediator to a sample.

The electron mediator that can be used is not particularly limited, and a known electron mediator can be used. The electron mediator is preferably water-soluble. In particular, when at least one selected from the group consisting of flavin mononucleotide, riboflavin, and 2-hydroxy-1,4-napthoquinone (HNQ) is included, a larger generation current (density) is obtained.

In particular, a study by the present inventors revealed that when the electron mediator includes HNQ, surprisingly, the generation current derived from Pg bacteria is significantly increased in bacteria in oral cavities. This suggests that even when *Porphyromonas gingivalis* (Pg bacteria), *Streptococcus mutans* (Sm bacteria), and Capnocytophaga *ochracea* (Co bacteria) are present together in a sample, the generation current specific to Pg bacteria can be detected.

Cases of samples including a glucogenic amino acid and an electron mediator have been described above, but in the in vitro diagnostic method, as long as the electrochemical measurement is performed in the presence of a glucogenic amino acid and an electron mediator, the form of adding the glucogenic amino acid and the electron mediator to a sample is not essential. In such a case, for example, a glucogenic amino acid may be fixed on the electrode surface.

As the method of the electrochemical measurement, a method by controlling the potential of the electrode and measuring the current as a function of time is preferable. Examples of such a method include an amperometry method, a cyclic voltammetry method, a linear sweep voltammetry method, and a square wave voltammetry method.

The material of the electrode is not particularly limited, and an electrode known for electrochemical measurement can be used. Examples of the material of the electrode include ITO (indium tin oxide), noble metals (such as gold (Au), silver (Ag), platinum (Pt), palladium (Pd), rhodium (Rh), iridium (Ir), and ruthenium (Ru)), copper (Cu), aluminum (Al), tungsten (W), molybdenum (Mo), chromium (Cr), titanium (Ti), nickel (Ni) and the like. The material may be a carbon material, such as carbon and graphite (graphene). In the point of view of a broad potential window, a boron-doped diamond electrode is also preferable.

In the electrochemical measurement, a general electrochemical measurement apparatus can be used. For example, a three-electrode type electrochemical measurement apparatus in which a working electrode, a counter electrode, and a reference electrode are accommodated in a cell can be used.

The temperature for performing the electrochemical measurement is not particularly limited, and the electrochemical measurement may be performed at a temperature similar to that at the sample collection site or may be performed at a controlled temperature. In such a case, the temperature of the sample is preferably 10° C. to 40° C.

The measurement may be performed in a general anaerobic glove box (anaerobic chamber) preferably in the absence of oxygen.

In order to receive electrons generated by anaerobic metabolism of periodontopathogenic bacteria and detect a current, the potential of an electrode (working electrode) is preferably controlled within a range greater than 0 V (vs. Ag/AgCl) and less than the upper limit of the potential window. From the viewpoint of easily obtaining a larger generation current or of easily generating a current within a shorter time, the potential of the electrode is preferably set to from 0 to +0.6 V (vs. Ag/AgCl).

When current generation is detected by this electrochemical measurement (Step S12: Yes), it is suggested that periodontopathogenic bacteria are present in a sample. In this case, information for judging that periodontal disease is progressing in the oral cavity of the subject is provided (Step S13).

In contrast, when no current generation is detected by this electrochemical measurement (Step S12: No), the diagnosis is finished, and information for judging that periodontal disease is progressing is not provided.

The information above is based on a measurement result, and the form thereof is not particularly limited, but when the information is information including at least one measurement result selected from the group consisting of a time from start of the electrochemical measurement to detection of the current generation and a maximum value of current density of the generated current (hereinafter, also referred to as "specific information"), the information is likely to become information that contributes to quantitative evaluation of the progress of periodontal disease and is therefore more preferable.

The specific information is a numerical value related to the content of the periodontopathogenic bacteria in a sample and is likely to become information that contributes to judgement of the degree or chronological progress of periodontal disease occurring in the oral cavity of a subject by, for example, comparing the value to the value of a healthy subject or to a past value of the same subject.

MODIFICATION EXAMPLE

A modification example of the in vitro diagnostic method according to the embodiment above is an in vitro diagnostic method of comparing the measurement result obtained when current generation is detected to a reference value and providing information including the comparison information as information for judging that periodontal disease is progressing in the oral cavity of the subject.

Examples of the reference value in this in vitro diagnostic method include the result by measurement by the same method using a sample of a healthy subject and a past test result of the same subject.

Examples of the comparison information include specific information by measurement by the same method using a sample of a healthy subject and a difference from specific information of the sample.

More specifically, examples of the comparison information include a difference between the time from start of the electrochemical measurement to detection of the current generation measured using a sample of a healthy subject by the same method and the time measured using a sample collected from a subject by the same method as above. If the time measured for the sample is shorter and the difference is larger, which can be information for judging that the sample contains more periodontopathogenic bacteria. The above comparison information is one example, and the information may be information other than the above.

[Pg Bacterium Detection Method]

The Pg bacterium detection method according to an embodiment of the present invention includes bringing a sample into contact with an electrode to perform electrochemical measurement in the presence of a glucogenic amino acid and 2-hydroxy-1,4-naphthoquinone under an anaerobic environment and providing information for judging that the sample contains *Porphyromonas gingivalis* when current generation is detected as a result of the electrochemical measurement.

As in Examples described later, the present inventors have confirmed experimentally that a large generation current specific to Pg bacteria can be detected by performing electrochemical measurement in the presence of a glucogenic amino acid and HNQ under an anaerobic environment.

For example, there is a strong desire for simple detection of the proliferative state of periodontopathogenic bacterium that is called "red complex" in the field of periodontal disease prevention and has a particularly large impact. As already described, the enzymatic method is not simple because the procedure is complicated and the results vary widely. However, according to the method above, Pg bacteria can be almost specifically detected by a very simple method.

Regarding the conditions for electrochemical measurement and so on, it is possible to apply the method that has been already described as the method of electrochemical measurement in the in vitro diagnostic method according to the first embodiment, and the preferable forms are the same. Accordingly, the description thereof is omitted.

The sample in the present detection method is not limited to that derived from the inside of an oral cavity of a subject and may be a sample cultured for test research, an environmental sample (water and dust), or the like. When a sample is not liquid, the sample can be used after extraction using water or the like and purification.

EXAMPLES

The present invention will now be described in more detail based on Examples. The materials, amount used, proportions, treatment details, treatment procedures, and so on shown in the following Examples can changed as appropriate without departing from the gist of the present invention. Accordingly, the scope of the present invention should not be construed to be limited by Examples shown below.

Influence of Glucogenic Amino Acid on Generation Current

Experiment 1: Reference Example

The influence of a glucogenic amino acid on current generation was verified using Pg bacteria. A total of 5 mL of a sample was subjected to measurement using a three-electrode electrochemical cell (working electrode: ITO, counter electrode: platinum, reference electrode: Ag/AgCl). The temperature was set to 37° C.

The sample used was prepared by adding 10 mM histidine or glucose to a DM liquid medium not containing yeast extract and further adding Pg bacteria solution ($OD_{600}$: 0.1) thereto. The measurement was performed in a COY anaerobic chamber filled with 100% nitrogen by chronoamperometry.

Figure 2:
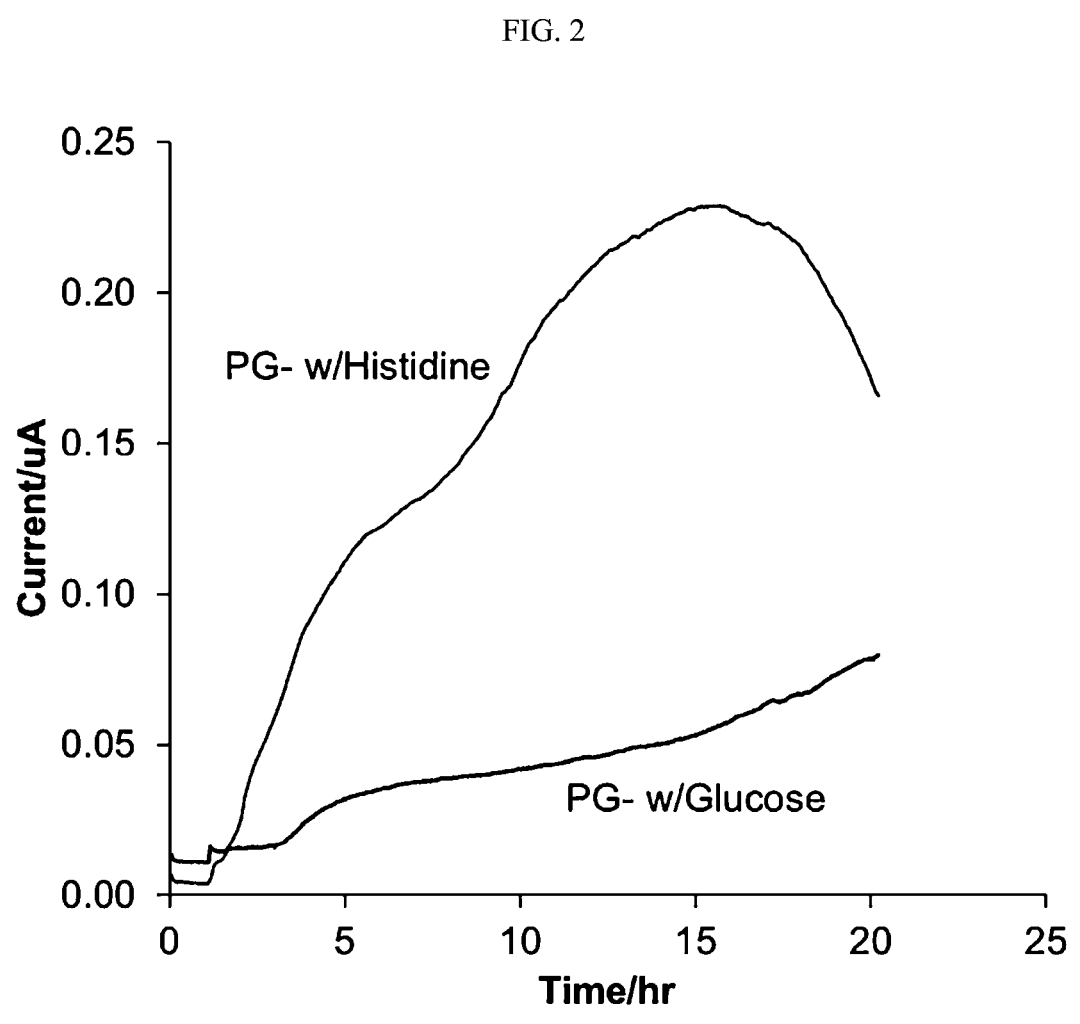

FIG. 2 is a chronoamperogram showing the influence of histidine on a generation current. "PG-w/Histidine" shows the results when a sample contains histidine as a glucogenic amino acid, and "PG-w/Glucose" shows the results when a sample does not contain histidine but instead contains glucose. As shown in FIG. 2, in the sample containing histidine, after the addition of Pg bacteria solution, current generation was promptly detected. In contrast, in the sample containing glucose, current generation was detected, but the magnitude thereof was smaller, and the time until the current generation was longer.

Experiment 2: Reference Example

Subsequently, a test was performed using aspartic acid or glutamic acid, instead of histidine, as the glucogenic amino acid. Aspartic acid and glutamic acid both have low solubility in water and were therefore dissolved in 0.5 M HCl. Accordingly, the pH of the DM liquid medium became 5.2 or less.

Figure 3:
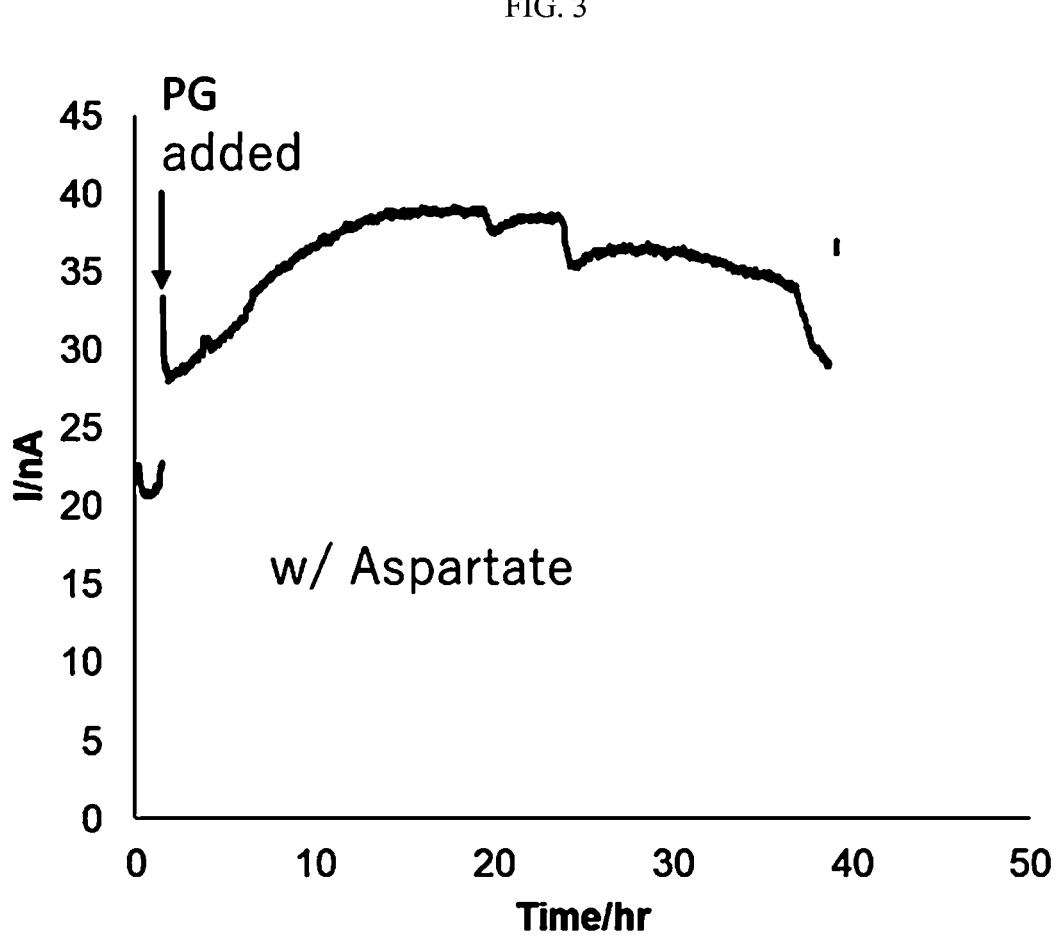
FIG. 3 is a chronoamperogram showing the influence of aspartic acid on a generation current.
Figure 4:
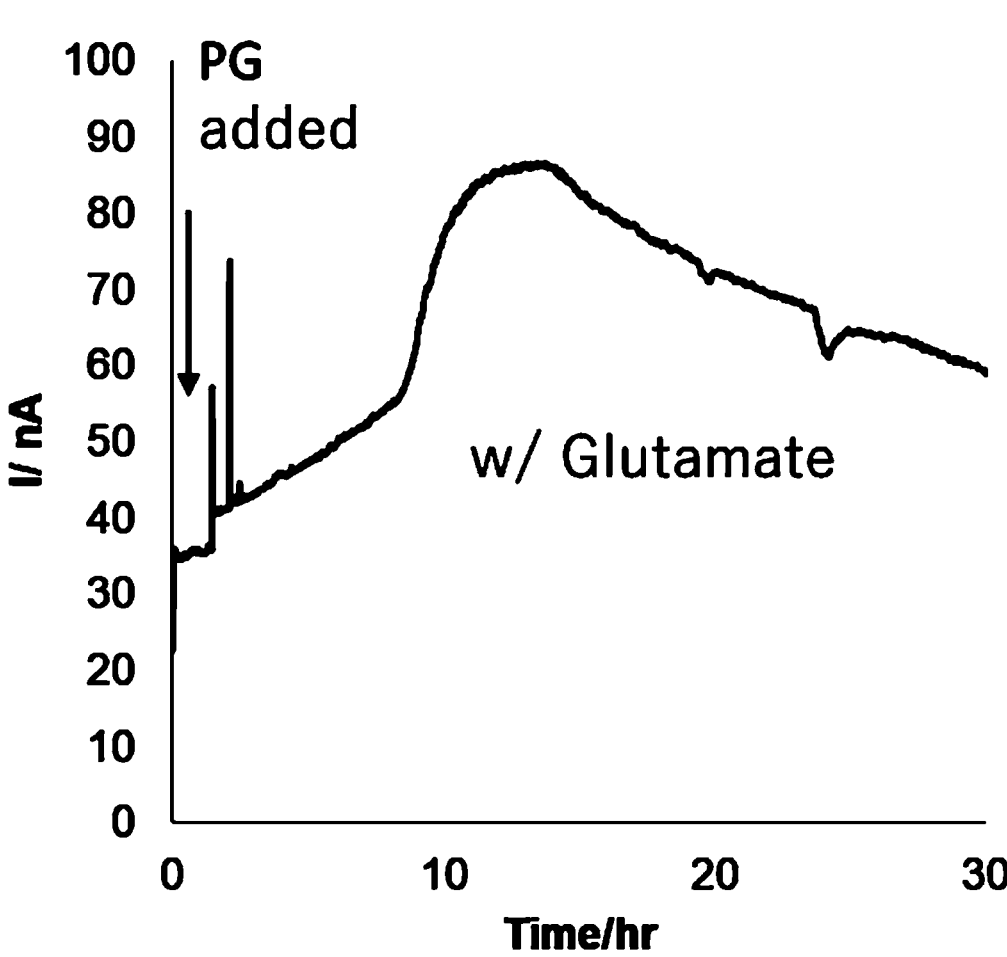
FIG. 4 is a chronoamperogram showing the influence of glutamic acid on a generation current.

FIG. 3 is a chronoamperogram showing the influence of aspartic acid on a generation current. FIG. 4 is a chronoamperogram showing the influence of glutamic acid on a generation current. In both cases, after the addition of Pg bacteria solution, current generation was promptly detected.

The results of FIGS. 2 to 4 demonstrate that when a sample contains a glucogenic amino acid, current generation was promptly detected by addition of Pg bacteria solution. In addition, when the glucogenic amino acid is histidine, the generation current was also larger and the time until the current generation was also shorter, compared to the cases of aspartic acid and glutamic acid.

Histidine Specific Current Generation by Pg Bacteria

Experiment 3: Reference Example

The generation current was investigated as in Example 1 except that Pg bacteria solution ($OD_{600}$: 0.5), *Streptococcus mutans* bacteria solution ($OD_{600}$: 0.5), and Capnocytophaga *ochracea* ($OD_{600}$: 0.5) were used instead of the Pg bacteria solution ($OD_{600}$: 0.1).

Figure 5:
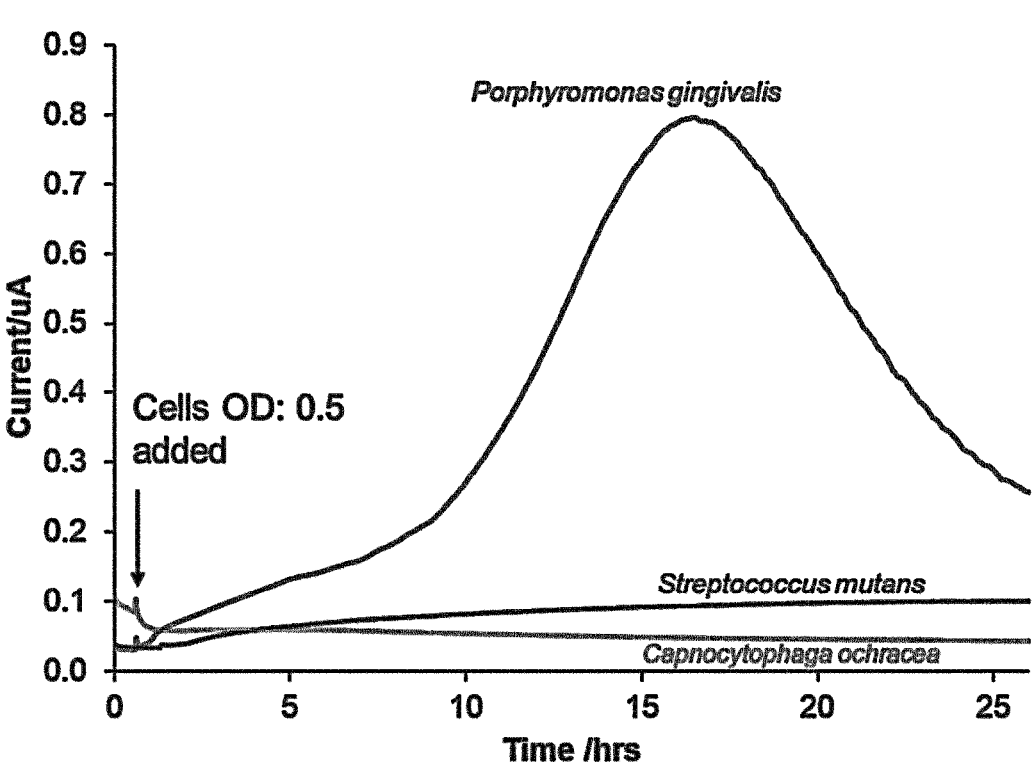
FIG. 5 is a graph showing Pg bacteria-specific current generation when aspartic acid was used as the glucogenic amino acid.

FIG. 5 shows the above results. FIG. 5 demonstrates that in a sample containing aspartic acid, current generation specific to Pg bacteria can be detected.

Influence of Electron Mediator on Current Generation

Experiment 4: Example

The influence of an electron mediator on current generation was investigated using an electrochemical measurement plate which was a 96-well plate having three electrodes printed on the bottom surface, instead of the three-electrode electrochemical cell (working electrode: ITO, counter electrode: platinum, reference electrode: Ag/AgCl).

The electron mediators used were HNQ, FMN, and RF at concentrations of 10 μM, 50 μM, and 100 μM, respectively. As the bacteria solution, Pg bacteria solution ($OD_{600}$: 0.5) was used, and other conditions were the same as those in Experiment 1.

Figure 6:
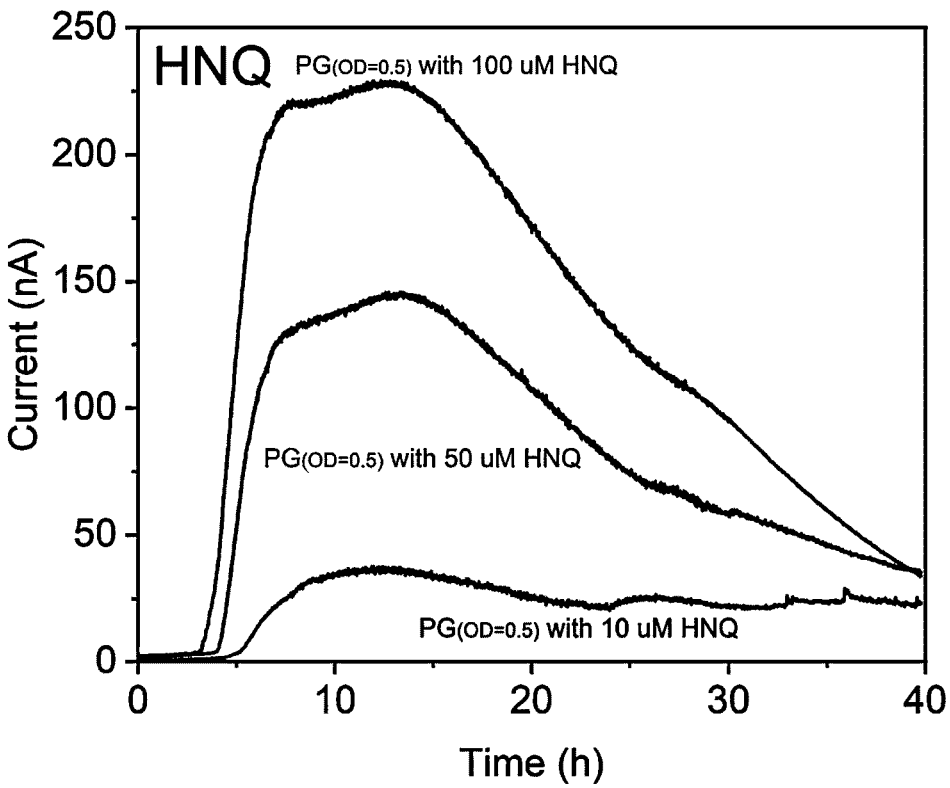
FIG. 6 shows the results of an experiment investigating the influence of HNQ on current generation.
Figure 7:
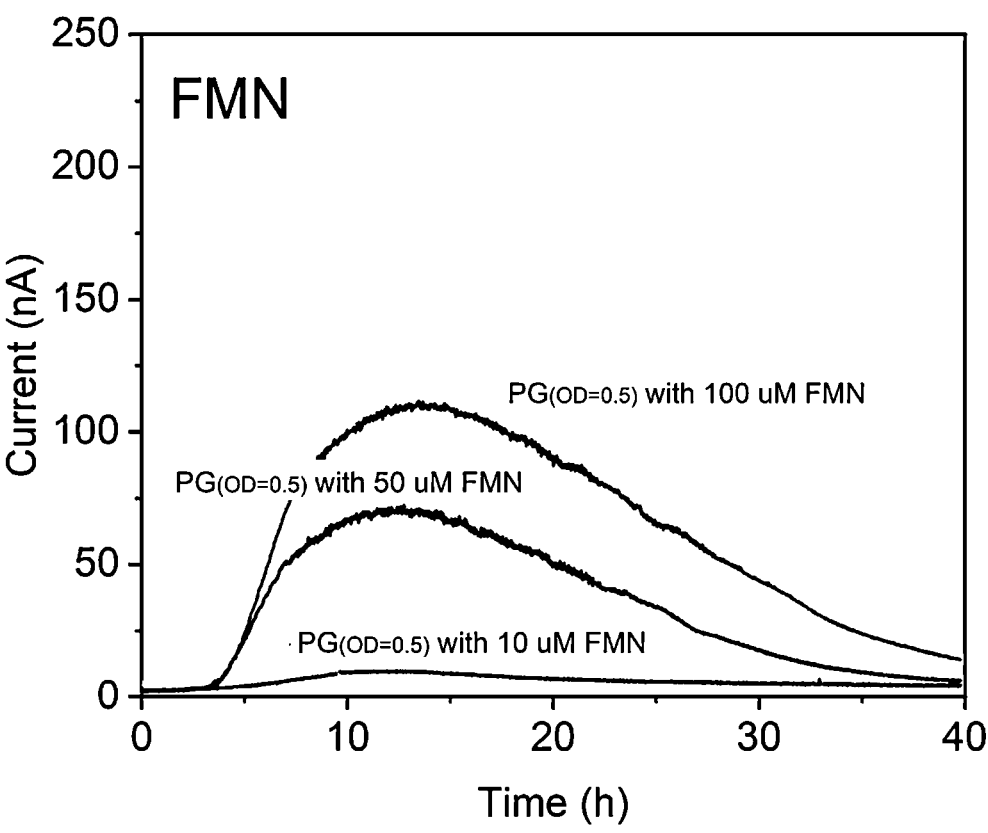
FIG. 7 shows the results of an experiment investigating the influence of FMN on current generation.
Figure 8:
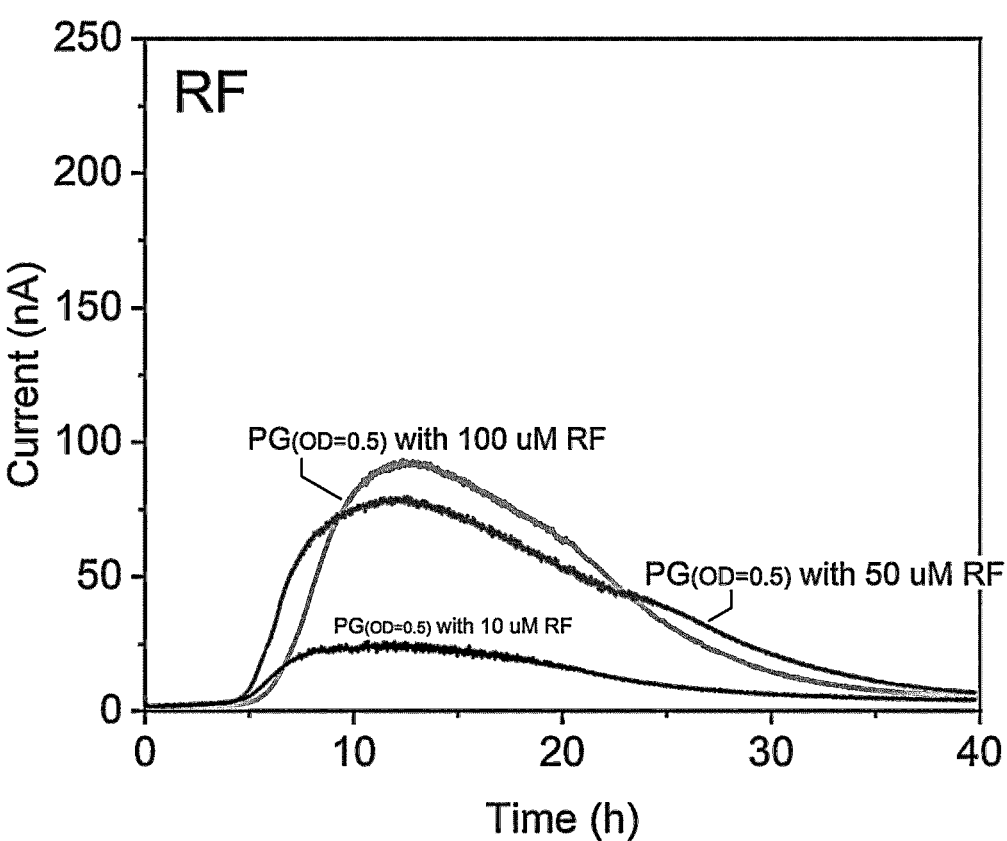
FIG. 8 shows the results of an experiment investigating the influence of RF on current generation.

FIGS. 6, 7, and 8 show the results of experiments using HNQ, FMN, and RF, respectively. In the results of FIGS. 6 to 8, also in using any of the electron mediators, after the addition of bacteria solution, a large current was promptly obtained (comparison with FIG. 2).

In particular, when HNQ was used, a larger current was obtained than when FMN or RF was used, and this tendency was significant particularly at a concentration greater than 10 μM.

INDUSTRIAL APPLICABILITY

According to the in vitro diagnostic method for periodontal disease of the present invention, saliva can be used as a sample, and information for judging the progress of periodontal disease can be obtained by a simple method. The information provided by the in vitro diagnostic method of the present invention can be used for not only determining the treatment policy by a dentist but also oral health care by a patient itself at home or in a remote location.

In addition, according to the Pg bacterium detection method of the present invention, current generation specific to Pg bacteria can be detected by using a combination of a glucogenic amino acid and HNQ. This method is useful not only for the decision of dental treatment policy but also in the research field.

The invention claimed is:

1. An in vitro diagnostic method for periodontal disease, comprising:
   bringing a sample derived from an oral cavity of a subject into contact with an electrode to perform electrochemical measurement in the presence of a glucogenic amino acid and an electron mediator under an anaerobic environment; and
   providing information for judging that periodontal disease is progressing in the oral cavity of the subject when a current generated by anaerobic metabolism of periodontopathogenic bacteria is detected as a result of the electrochemical measurement.

2. The in vitro diagnostic method for periodontal disease according to claim 1, wherein the glucogenic amino acid includes at least one selected from the group consisting of arginine, histidine, aspartic acid, and glutamic acid.

3. The in vitro diagnostic method for periodontal disease according to claim 1, wherein the electron mediator includes at least one selected from the group consisting of flavin mononucleotide, riboflavin, and 2-hydroxy-1,4-naphthoquinone.

4. The in vitro diagnostic method for periodontal disease according to claim 1, wherein the electron mediator is 2-hydroxy-1,4-naphthoquinone.

5. The in vitro diagnostic method for periodontal disease according to claim 1, wherein the method of the electrochemical measurement is a method by controlling a potential of the electrode and measuring a current flowing in the electrode as a function of time.

6. The in vitro diagnostic method for periodontal disease according to claim 5, wherein the potential is within a range of greater than 0 V with respect to a silver-silver chloride electrode and less than the upper limit of a potential window.

7. The in vitro diagnostic method for periodontal disease according to claim 1, wherein the information for judging includes at least one measurement result selected from the group consisting of a time from start of the electrochemical measurement to detection of the current generation and a maximum value of current density of the generated current.

8. The in vitro diagnostic method for periodontal disease according to claim 7, wherein the information for judging includes comparison information between a predetermined reference value and the measurement result.

9. The in vitro diagnostic method for periodontal disease according to claim 1, wherein the periodontal disease comprises pathogenic bacteria, wherein the pathogenic bacteria of the periodontal disease includes *Porphyromonas gingivalis*.

10. A *Porphyromonas gingivalis* (Pg) bacterium detection method comprising:

bringing a sample into contact with an electrode to perform electrochemical measurement in the presence of a glucogenic amino acid and 2-hydroxy-1,4-naphthoquinone under an anaerobic environment; and providing information for judging that Pg is contained in the sample when current generation is detected as a result of the electrochemical measurement.

11. The Pg bacterium detection method according to claim 10, wherein a method of the electrochemical measurement is a method including the steps of controlling a potential of the electrode and measuring a current flowing in the electrode as a function of time.

12. The Pg bacterium detection method according to claim 11, wherein the potential is within a range of greater than 0 V with respect to a silver-silver chloride electrode and less than the upper limit of a potential window.

13. The Pg bacterium detection method according to claim 10, wherein the information for judging includes at least one measurement result selected from the group consisting of a time from start of the electrochemical measurement to detection of the current generation and a maximum value of current density of the generated current.

14. The Pg bacterium detection method according to claim 13, wherein the information for judging includes comparison information between a predetermined reference value and the measurement result.

15. The in vitro diagnostic method for periodontal disease according to claim 3, wherein the periodontal disease comprises pathogenic bacteria, wherein the pathogenic bacteria of the periodontal disease includes Pg.

16. The in vitro diagnostic method for periodontal disease according to claim 4, wherein the periodontal disease comprises pathogenic bacteria, wherein the pathogenic bacteria of the periodontal disease includes Pg.

17. The in vitro diagnostic method for periodontal disease according to claim 3, wherein a method of the electrochemical measurement is a method including the steps of controlling a potential of the electrode and measuring a current flowing in the electrode as a function of time.

18. The in vitro diagnostic method for periodontal disease according to claim 17, wherein the potential is within a range of greater than 0 V with respect to a silver-silver chloride electrode and less than the upper limit of a potential window.

19. The in vitro diagnostic method for periodontal disease according to claim 18, wherein the electron mediator is 2-hydroxy-1,4-naphthoquinone.

20. The in vitro diagnostic method for periodontal disease according to claim 19, wherein the periodontal disease comprises pathogenic bacteria, wherein the pathogenic bacteria of the periodontal disease includes Pg.

* * * * *